United States Patent
Al-Ali

(10) Patent No.: US 7,355,512 B1
(45) Date of Patent: Apr. 8, 2008

(54) PARALLEL ALARM PROCESSOR

(75) Inventor: Ammar Al-Ali, Tustin, CA (US)

(73) Assignee: Masimo Corporation, Irvine, CA (US)

( * ) Notice: Subject to any disclaimer, the term of this patent is extended or adjusted under 35 U.S.C. 154(b) by 0 days.

(21) Appl. No.: 11/717,591

(22) Filed: Mar. 13, 2007

Related U.S. Application Data

(63) Continuation of application No. 11/405,815, filed on Apr. 18, 2006, now Pat. No. 7,190,261, which is a continuation of application No. 10/975,860, filed on Oct. 28, 2004, now Pat. No. 7,030,749, which is a continuation of application No. 10/351,735, filed on Jan. 24, 2003, now Pat. No. 6,822,564.

(60) Provisional application No. 60/351,510, filed on Jan. 24, 2002.

(51) Int. Cl.
*G08B 29/00* (2006.01)

(52) U.S. Cl. .............. 340/511; 340/539.12; 340/573.1; 600/322; 600/323

(58) Field of Classification Search ................ 340/511, 340/539.12, 573.1; 600/322, 323
See application file for complete search history.

(56) References Cited

U.S. PATENT DOCUMENTS

| | | |
|---|---|---|
| 4,245,648 A | 1/1981 | Trimmer et al. |
| 4,960,128 A | 10/1990 | Gordon et al. |
| 4,964,408 A | 10/1990 | Hink et al. |
| 5,041,187 A | 8/1991 | Hink et al. |
| 5,069,213 A | 12/1991 | Polczynski |
| 5,163,438 A | 11/1992 | Gordon et al. |
| 5,298,021 A | 3/1994 | Sherer |
| 5,337,744 A | 8/1994 | Branigan |
| 5,341,805 A | 8/1994 | Stavridi et al. |
| D353,195 S | 12/1994 | Savage et al. |
| D353,196 S | 12/1994 | Savage et al. |
| 5,377,676 A | 1/1995 | Vari et al. |
| D359,546 S | 6/1995 | Savage et al. |
| 5,431,170 A | 7/1995 | Mathews |
| D361,840 S | 8/1995 | Savage et al. |
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| 5,482,036 A | 1/1996 | Diab et al. |
| 5,490,505 A | 2/1996 | Diab et al. |
| 5,494,043 A | 2/1996 | O'Sullivan et al. |
| 5,533,511 A | 7/1996 | Kaspari et al. |
| 5,561,275 A | 10/1996 | Savage et al. |
| 5,562,002 A | 10/1996 | Lalin |

(Continued)

*Primary Examiner*—Jeffery Hofsass
*Assistant Examiner*—Samuel J. Walk
(74) *Attorney, Agent, or Firm*—Knobbe, Martens, Olson & Bear, LLP

(57) ABSTRACT

A parallel alarm processor has a threshold detector, a pattern extractor, a predetermined reference pattern, a first alarm and a second alarm. The threshold detector has a first output responsive to relatively long duration oxygen desaturations. The pattern extractor has a second output responsive to relatively short duration oxygen desaturations. The predetermined reference pattern is indicative of a series of intermittent oxygen desaturations. A first alarm is triggered when the first output crosses a lower limit threshold. A second alarm is triggered when the second output matches the predetermined reference pattern. In an embodiment, an integrator inputs smoothed oxygen saturation measurements to the threshold detector, and a predictor inputs predictive oxygen saturation measurements to the pattern extractor.

9 Claims, 9 Drawing Sheets

U.S. PATENT DOCUMENTS

| | | |
|---|---|---|
| 5,590,649 A | 1/1997 | Caro et al. |
| 5,602,924 A | 2/1997 | Durand et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,685,299 A | 11/1997 | Diab et al. |
| D393,830 S | 4/1998 | Tobler et al. |
| 5,743,262 A | 4/1998 | Lepper, Jr. et al. |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,819,007 A | 10/1998 | Elghazzawi |
| 5,823,950 A | 10/1998 | Diab et al. |
| 5,830,131 A | 11/1998 | Caro et al. |
| 5,833,618 A | 11/1998 | Caro et al. |
| 5,860,918 A | 1/1999 | Schradi et al. |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,995,855 A | 11/1999 | Kiani et al. |
| 5,997,343 A | 12/1999 | Mills et al. |
| 6,002,952 A | 12/1999 | Diab et al. |
| 6,011,986 A | 1/2000 | Diab et al. |
| 6,027,452 A | 2/2000 | Flaherty et al. |
| 6,036,642 A | 3/2000 | Diab et al. |
| 6,045,509 A | 4/2000 | Caro et al. |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,124,597 A | 9/2000 | Shehada |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,285,896 B1 | 9/2001 | Tobler et al. |
| 6,321,100 B1 | 11/2001 | Parker |
| 6,331,159 B1 | 12/2001 | Amano et al. |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,430,525 B1 | 8/2002 | Weber et al. |
| 6,463,311 B1 | 10/2002 | Diab |
| 6,470,199 B1 | 10/2002 | Kopotic et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,537,214 B1 | 3/2003 | Hood et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,639,668 B1 | 10/2003 | Trepagnier |
| 6,640,116 B2 | 10/2003 | Diab |
| 6,643,530 B2 | 11/2003 | Diab et al. |
| 6,650,917 B2 | 11/2003 | Diab et al. |
| 6,654,624 B2 | 11/2003 | Diab et al. |
| 6,658,277 B2 | 12/2003 | Diab et al. |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,745,060 B2 | 6/2004 | Diab et al. |
| 6,760,607 B2 | 7/2004 | Al-Ali |
| 6,770,028 B1 | 8/2004 | Ali et al. |
| 6,771,994 B2 | 8/2004 | Kiani et al. |
| 6,792,300 B1 | 9/2004 | Diab et al. |
| 6,813,511 B2 | 11/2004 | Diab et al. |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,993,371 B2 | 1/2006 | Kiani et al. |
| 6,996,427 B2 | 2/2006 | Ali et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |

| | | | | | |
|---|---|---|---|---|---|
| 7,044,918 B2 | 5/2006 | Diab | 7,215,984 B2 | 5/2007 | Diab |
| 7,067,893 B2 | 6/2006 | Mills et al. | 7,215,986 B2 | 5/2007 | Diab |
| 7,096,052 B2 | 8/2006 | Mason et al. | 7,221,971 B2 | 5/2007 | Diab |
| 7,096,054 B2 | 8/2006 | Abdul-Hafiz et al. | 7,225,006 B2 | 5/2007 | Al-Ali et al. |
| 7,132,641 B2 | 11/2006 | Schulz et al. | 7,225,007 B2 | 5/2007 | Al-Ali |
| 7,142,901 B2 | 11/2006 | Kiani et al. | RE39,672 E | 6/2007 | Shehada et al. |
| 7,149,561 B2 | 12/2006 | Diab | 7,239,905 B2 | 7/2007 | Kiani-Azarbayjany et al. |
| 7,186,966 B2 | 3/2007 | Al-Ali | 2003/0004421 A1 | 1/2003 | Ting et al. |
| 7,190,261 B2 | 3/2007 | Al-Ali | 2003/0107487 A1 | 6/2003 | Korman et al. |

PARALLEL ALARM PROCESSOR

CROSS-REFERENCE TO RELATED APPLICATIONS

This application is a CON of 11/405,815 filed Apr. 18, 2006 now U.S. Pat. No. 7,190,261, which is a CON of 10/975,860 filed Oct. 28, 2004 now U.S. Pat. No. 7,030,749, which is a CON of 10/351,735 filed on Jan. 24, 2003 now U.S. Pat. No. 6,822,564, which claims the benefit of 60/351,510 filed Jan. 24, 2002. This application also incorporates the foregoing patents and provisional patent application herein by reference.

BACKGROUND OF THE INVENTION

Physiological measurement instruments employed in healthcare environments often feature visual and audible alarm mechanisms that alert a caregiver when a patient's vital signs are outside of predetermined limits. One example is a pulse oximeter, which measures the oxygen saturation level of arterial blood, an indicator of oxygen supply. A typical pulse oximeter displays a numerical readout of the patient's oxygen saturation, a numerical readout of pulse rate, and a plethysmograph, which is indicative of a patient's pulse. In addition, a pulse oximeter provides an alarm that warns of a potential desaturation event.

FIG. 1 illustrates a prior art pulse oximeter portion 100 having a signal input 101 and generating an oxygen saturation measurement output 103 and an alarm output 105. The pulse oximeter portion 100 has an oxygen saturation ($SpO_2$) processor 110 and an associated threshold detector 120. The $SpO_2$ processor 110 derives an oxygen saturation measurement from the signal input 101. The signal input 101 is typically an amplified, filtered, digitized and demodulated sensor signal. A sensor emits both red and infrared (IR) wavelength light, which is transmitted through a patient's tissue, detected and input to the pulse oximeter. The pulse oximeter calculates a normalized ratio (AC/DC) of the detected red and infrared intensities, and an arterial oxygen saturation value is empirically determined based on a ratio of these normalized ratios, as is well-known in the art. The oxygen saturation measurement output 103 is typically a digital signal that is then communicated to a display.

FIG. 2 illustrates the operation of a conventional threshold detector 120 (FIG. 1) utilizing a graph 200 of oxygen saturation 201 versus time 202. The graph 200 displays a particular oxygen saturation measurement 210 corresponding to the measurement output 103 (FIG. 1) and a predetermined alarm threshold 206. During an alarm time period 270 when the measured oxygen saturation 210 is below the threshold 206, an alarm output 105 (FIG. 1) is generated, which triggers a caregiver alert. Adjusting the threshold 206 to a lower value of oxygen saturation 201 reduces the probability of an alarm, i.e. reduces the probability of a false alarm and increases the probability of a missed event. Likewise, adjusting the threshold 206 to a higher value of oxygen saturation 201 increases the probability of an alarm, i.e. increases the probability of a false alarm and decreases the probability of a missed event.

SUMMARY OF THE INVENTION

One performance measure for a physiological measurement instrument is the probability of a false alarm compared with the probability of a missed event. Missed events, such as an oxygen desaturation when measuring oxygen saturation, may detrimentally effect patient health. False alarms waste caregiver resources and may also result in a true alarm being ignored. It is desirable, therefore, to provide an alarm mechanism to reduce the probability of false alarms without significantly increasing the probability of missed events, and, similarly, to reduce the probability of missed events without significantly increasing the probability of false alarms.

An alarm processor has a signal input responsive to a physiological parameter and a plurality of parameter processors responsive to the signal input so as to provide a plurality of measurements of the parameter having differing characteristics. In addition, the alarm processor has an alarm condition applicable to at least one of the measurements so as to define a limit for the parameter. Further, the alarm processor has an alarm indicator operating on the measurements and the alarm condition so as to provide an alarm output that changes state to indicate that the parameter may have exceeded the limit.

One aspect of a parallel alarm processor comprises a sensor signal, first and second processors, a threshold detector and a pattern processor. The sensor signal is responsive to multiple wavelengths of light transmitted into a tissue site and detected after attenuation by pulsatile blood flow within the tissue site. The first processor has an input responsive to the sensor signal and a smoothing output responsive to relatively long duration oxygen desaturations. The second processor has an input responsive to the sensor signal and a predictor output responsive to relatively short duration, intermittent oxygen desaturations. The threshold detector is responsive to the smoothing output so as to generate a first alarm when the smoothing output crosses a predetermined threshold. The pattern processor is responsive to the predictor output so as to generate a second alarm when a predetermined pattern is detected in a series of oxygen desaturations. In an embodiment, the pattern processor has a memory, an extractor and a comparator. The memory stores a predetermined reference pattern. The extractor generates an extracted pattern of oxygen desaturations from the predictor output. The comparator is communications with the memory and the extractor so as to trigger the second alarm when the reference pattern generally matches the extracted pattern. In an embodiment, the first and second processors are a variable mode averager.

Another aspect of a parallel alarm processor is a method comprising transmitting light having multiple wavelengths into a patient tissue site and detecting the light after attenuation by pulsatile arterial blood flow within the tissue site so as to generate a sensor signal. A first blood oxygen saturation measurement is generated that is responsive to the sensor signal and to long duration oxygen desaturations of the patient. A second oxygen saturation measurement is generated responsive to the sensor signal and to short duration, intermittent oxygen desaturations of the patient. A threshold crossing of the smoother blood oxygen saturation measurement is detected. A pattern in the second blood oxygen saturation measurement is recognized. A first alarm is triggered in response to the recognized pattern and a second alarm is triggered in response to the threshold crossing. In an embodiment, the first blood oxygen saturation measurement is a smoothed oxygen saturation parameter and the second blood oxygen saturation measurement is a predicted oxygen saturation parameter.

A further aspect of a parallel alarm processor comprises a threshold detector, a pattern extractor, a predetermined reference pattern, a first alarm and a second alarm. The threshold detector has a first output responsive to relatively long duration oxygen desaturations. The pattern extractor has a second output responsive to relatively short duration oxygen desaturations. The predetermined reference pattern is indicative of a series of intermittent oxygen desaturations. A first alarm is triggered when the first output crosses a lower limit threshold. A second alarm is triggered when the second output matches the predetermined reference pattern. In an embodiment, an integrator inputs smoothed oxygen saturation measurements to the threshold detector, and a predictor inputs predictive oxygen saturation measurements to the pattern extractor. In an embodiment, the integrator and the predictor are a variable mode averager.

DETAILED DESCRIPTION OF THE PREFERRED EMBODIMENTS

Figure 3:
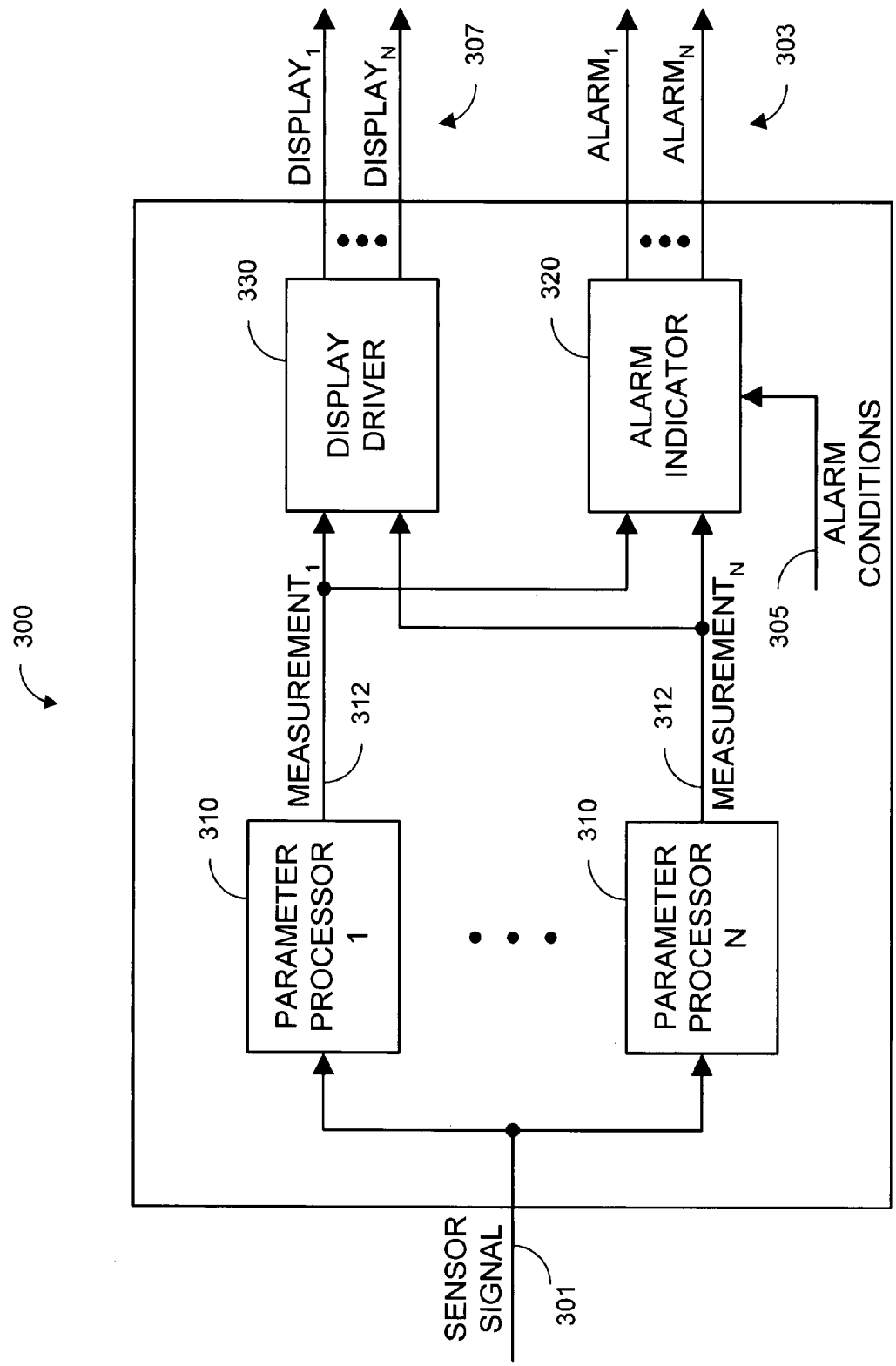
FIG. 3 is a block diagram of an alarm processor utilizing parallel measurements of a physiological parameter.

FIG. 3 illustrates a parallel measurement alarm processor 300. The alarm processor 300 has a sensor signal input 301 responsive to a physiological parameter and provides one or more alarm outputs 303 to indicate that the physiological parameter may have exceeded particular limits. The alarm processor 300 also has multiple parameter processors 310, which do not necessarily have the same or similar internal configurations. The multiple parameter processors 310 input the sensor signal 301 and provide parallel measurements 312 of the physiological parameter, each measurement having differing characteristics, such as response time or bandwidth to name a few. The alarm processor 300 further has an alarm indicator 320 that inputs the parallel parameter measurements 312 and generates the alarm outputs 303 based upon alarm conditions 305. The alarm outputs 303 change state to indicate that the parameter may have exceed one or more limits and to trigger an alarm accordingly. The alarm conditions 305 define particular limits with respect to one or more of the measurements 312. The alarm conditions 305 may be predefined, such as by user input, or determined by a separate process, such as a measurement of sensor signal quality or data confidence as described in U.S. patent application Ser. No. 09/858,114 entitled "Pulse Oximetry Data Confidence Indicator," assigned to Masimo Corporation, Irvine, Calif. and incorporated by reference herein. The alarm processor 300 may also have a display driver 330 that processes one or more of the parameter measurements 312 and provides one or more display outputs 307.

Figure 1:
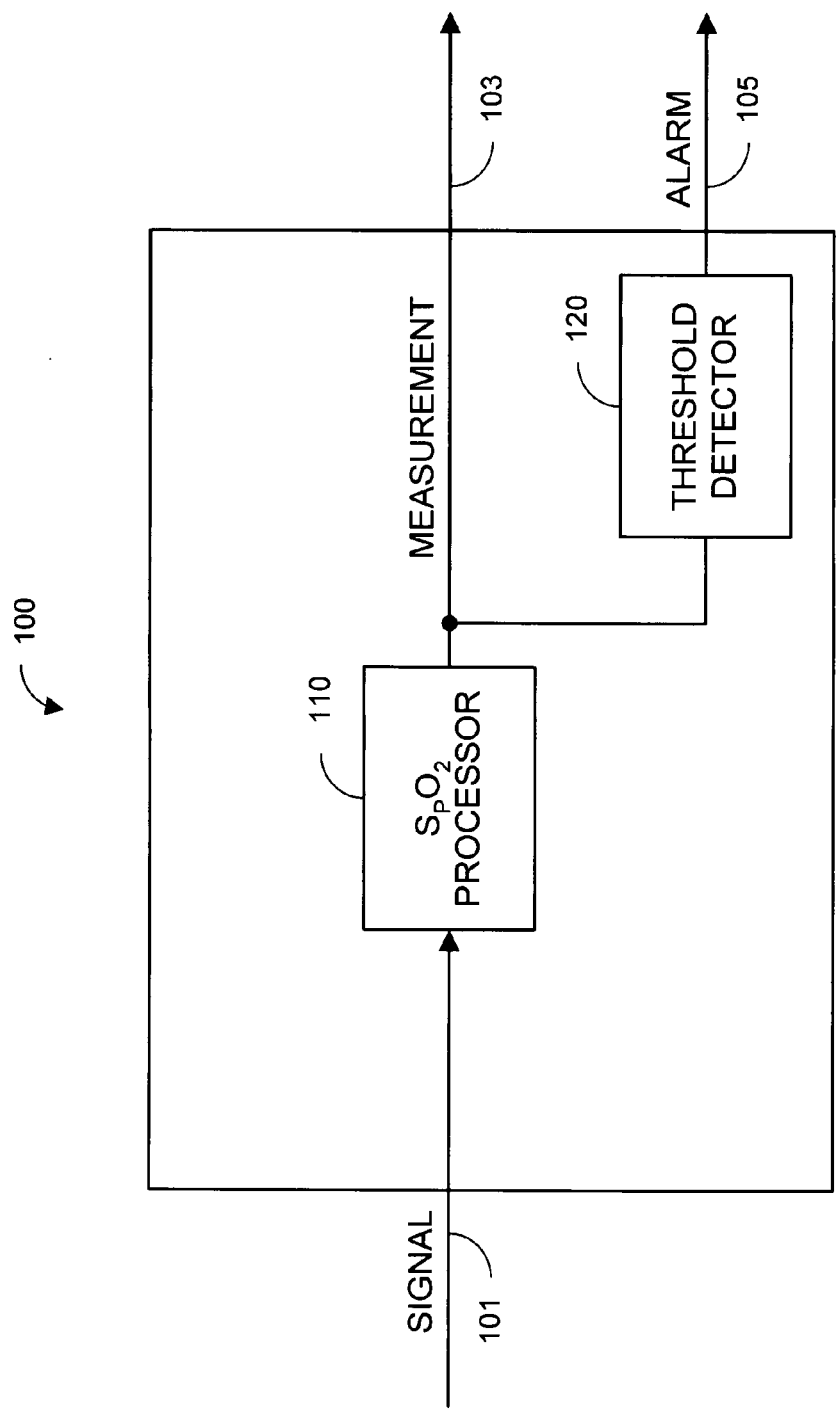
FIG. 1 is a block diagram of a prior art pulse oximeter portion.
Figure 2:
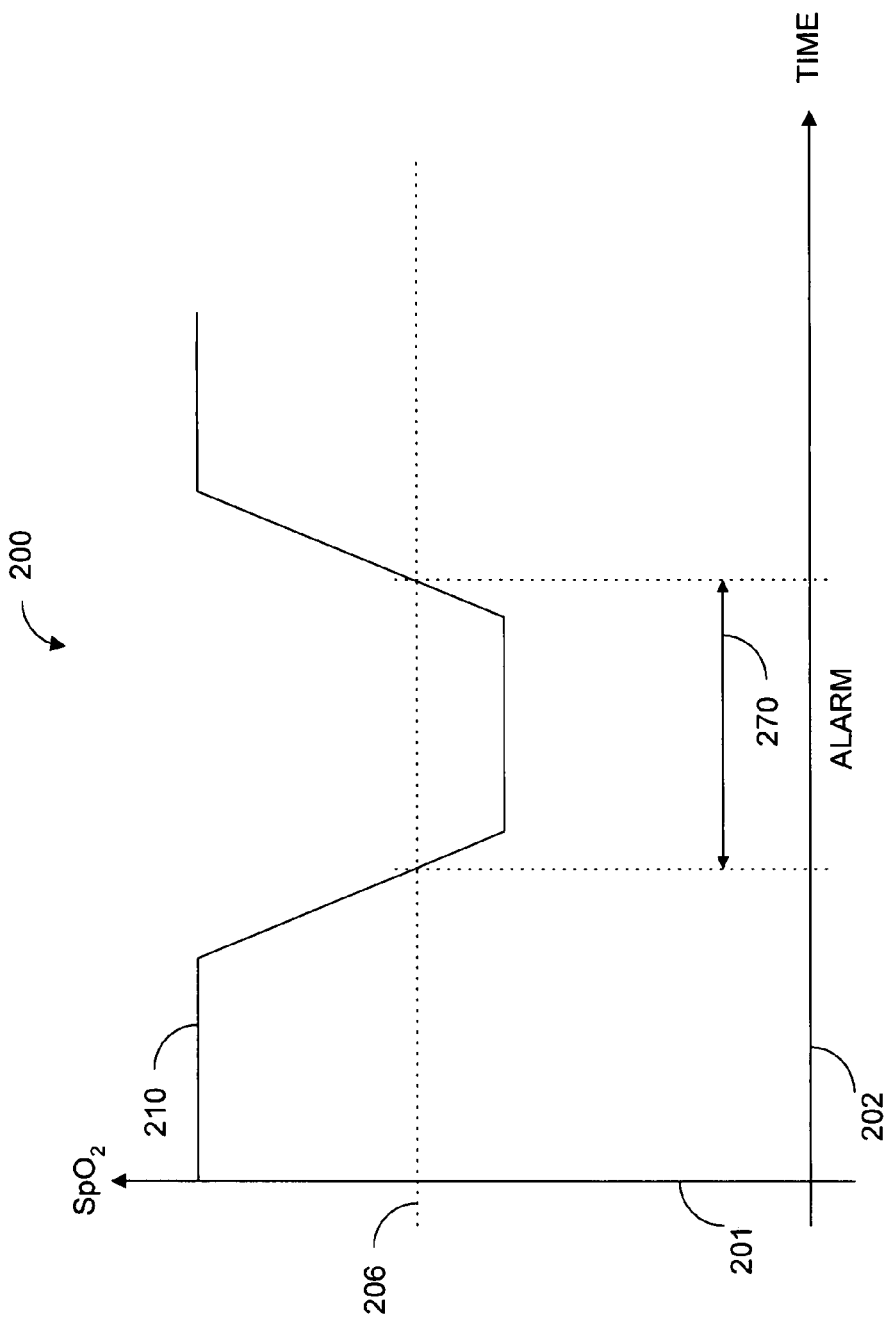
FIG. 2 is a graph of oxygen saturation versus time illustrating a conventional threshold detector alarm.
Figure 4:
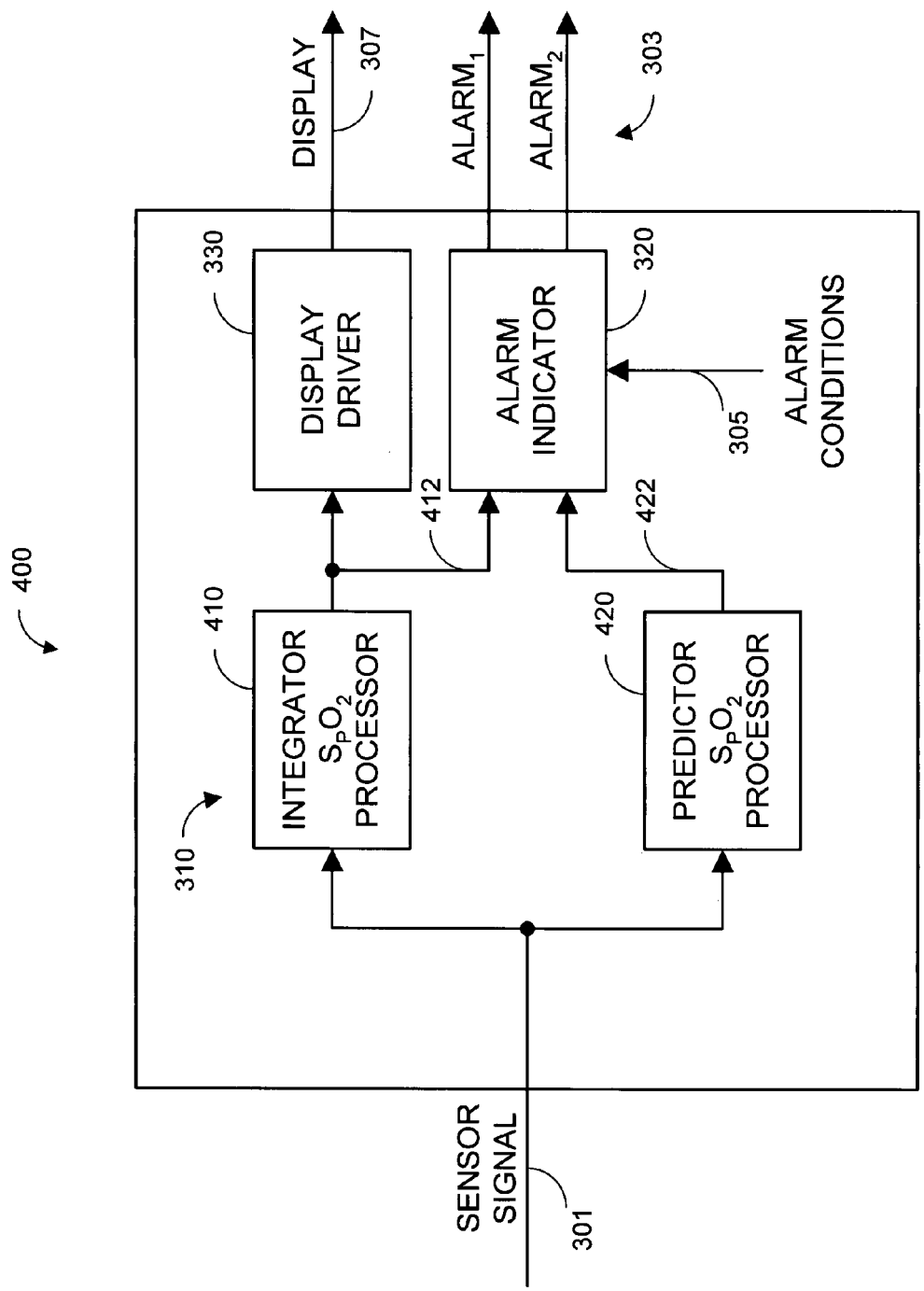
FIG. 4 is a block diagram of a pulse oximeter processor utilizing dual oxygen saturation measurements.

FIG. 4 illustrates a pulse oximeter embodiment 400 of the alarm processor 300 (FIG. 3) described above. A pulse oximeter sensor (not shown) provides a signal input 301 that is responsive to arterial oxygen saturation, as described with respect to FIG. 1, above. The alarm processor 400 has dual oxygen saturation processors 310. An integrator oxygen saturation (SpO$_2$) processor 410 outputs a slow SpO$_2$ measurement 412, i.e. a measurement having a slow response time to changes in the SpO$_2$ parameter. A predictor SpO$_2$ processor 420 outputs a fast SpO$_2$ measurement 422, i.e. a measurement having a fast response time that tracks changes in the SpO$_2$ parameter. The slow SpO$_2$ measurement 412 is input to a display driver 330, which provides an oxygen saturation display output 307. For example, the display output 307 may be input to a digital display that provides a numerical readout of oxygen saturation to a caregiver. Both the slow SpO$_2$ measurement 412 and the fast SpO$_2$ measurement 422 are input to an alarm indicator 320 that generates at least one alarm output 303 based upon alarm conditions 305, as described in further detail with respect to FIGS. 5-8, below.

The integrator SpO$_2$ processor 410, advantageously, provides a smoothed measurement of oxygen saturation suitable for threshold detection. The predictor SpO$_2$ processor 420, advantageously, provides a curve-fitting or a predictive measurement of oxygen saturation that detects trends in oxygen saturation, as described in further detail with respect to FIG. 5 and FIGS. 6A-B, below. Further, the predictor SpO$_2$ processor 420 advantageously tracks oxygen saturation details that may signal a critical physiological event, as described in further detail with respect to FIGS. 7-8, below. The integrator SpO$_2$ processor 410 and predictor SpO$_2$ processor 420 may be a pulse oximeter as described in U.S. patent application Ser. No. 09/586,845 entitled "Variable Mode Averager," assigned to Masimo Corporation, Irvine, Calif. and incorporated by reference herein.

Figure 5:
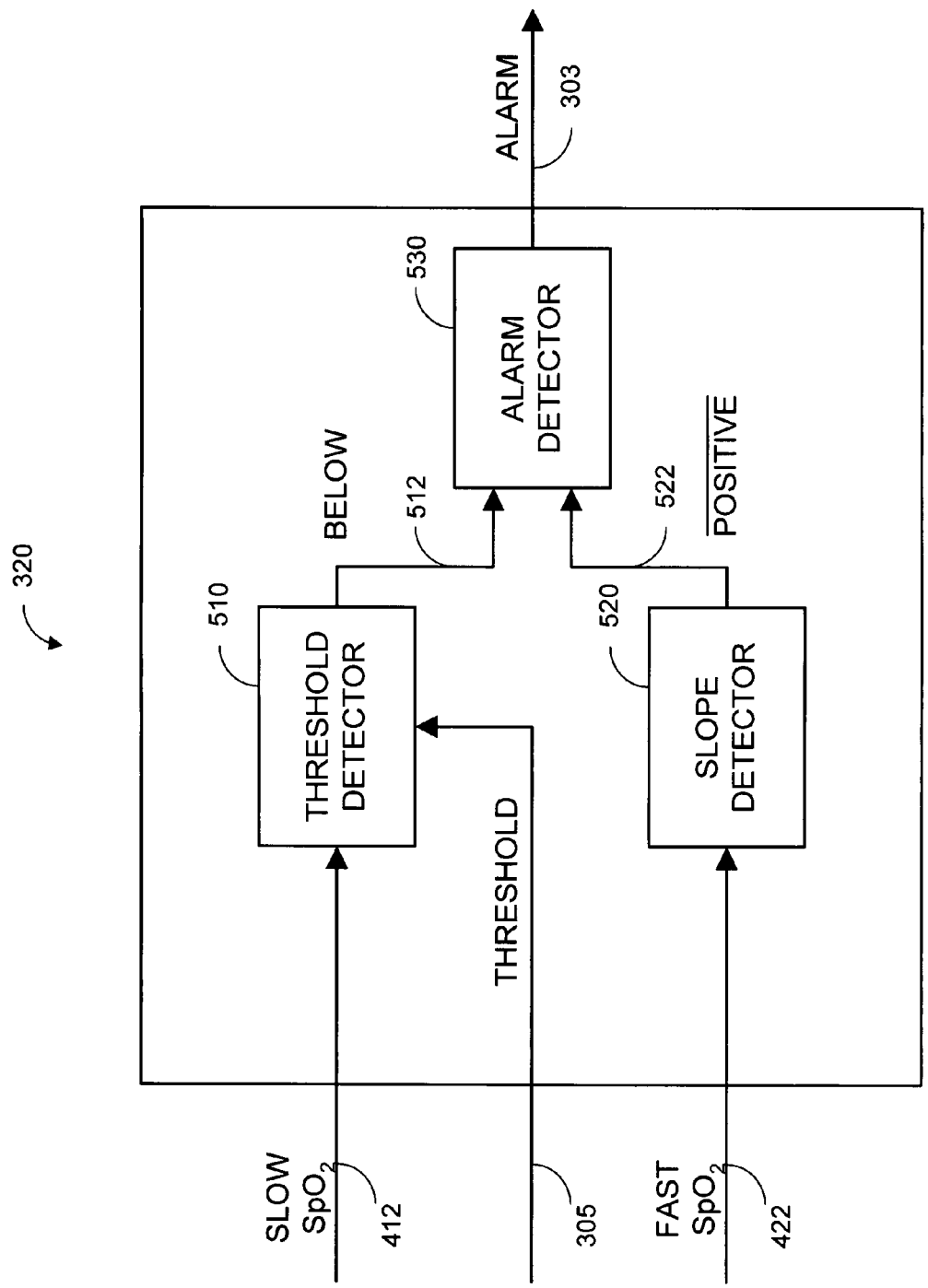
FIG. 5 is a block diagram of a predictive alarm indicator utilizing a threshold detector with a slow oxygen saturation measurement input and a slope detector with a fast oxygen saturation measurement input.

FIG. 5 illustrates a trend embodiment of an alarm indicator 320, which has a threshold detector 510, a slope detector 520 and alarm detector 530. The threshold detector 510 has a slow SpO$_2$ measurement 412 and a threshold alarm condition 305 as inputs and a logic output BELOW 512. The slope detector 520 has a fast SpO$_2$ measurement 422 input and a logic output POSITIVE/522. The alarm detector 530 has BELOW 512 and POSITIVE/522 logic inputs and generates an alarm output 303. The threshold detector 510 is a comparator that asserts BELOW 512 while the slow SpO$_2$ measurement 412 is less in value than the value of the threshold 305. The slope detector 520 is a differentiator and comparator that asserts POSITIVE/522 while the slope of the fast SpO$_2$ measurement 422 is non-positive, i.e. while the derivative of the fast SpO$_2$ measurement 422 is zero or less than zero. The alarm detector 530 performs a logical AND function, asserts the alarm output 303 and indicates an alarm when BELOW 512 and POSITIVE/522 are both asserted. In this manner, an alarm output 303 only changes state when the slow SpO$_2$ measurement 412 is below a threshold 305 and the fast SpO$_2$ measurement 422 has not begun to increase in value. Advantageously, the trend recognition alarm indicator 320 reduces false alarms by suppressing a threshold-based alarm on the slow SpO$_2$ measurement 412 when the fast SpO$_2$ measurement 422 determines that a patient's oxygen saturation is in recovery, as described in further detail with respect to FIGS. 6A-B, below.

Figure 6A:
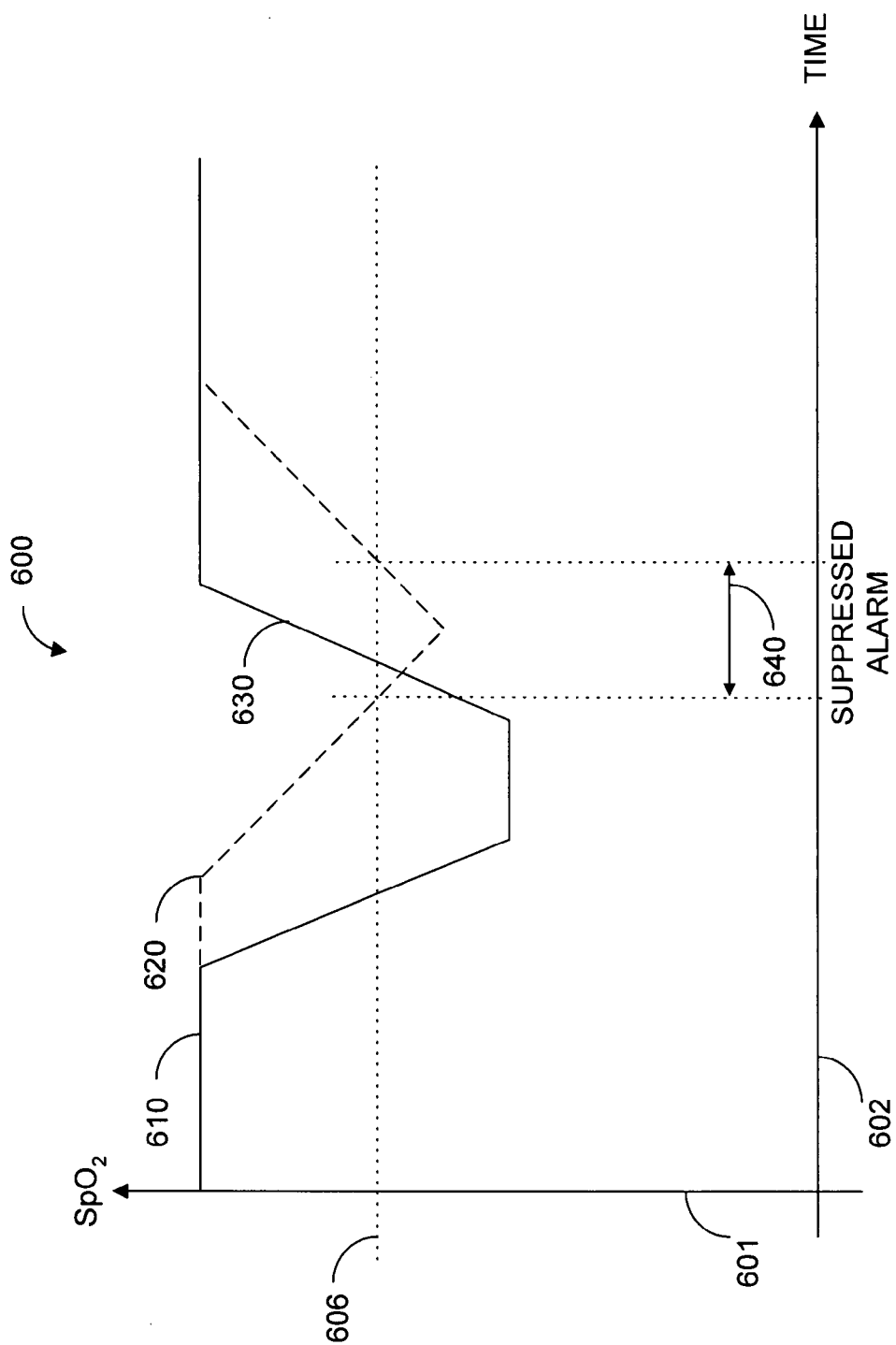
FIGS. 6A-B are graphs of oxygen saturation versus time illustrating operation of the alarm indicator according to FIG. 5.
Figure 6B:
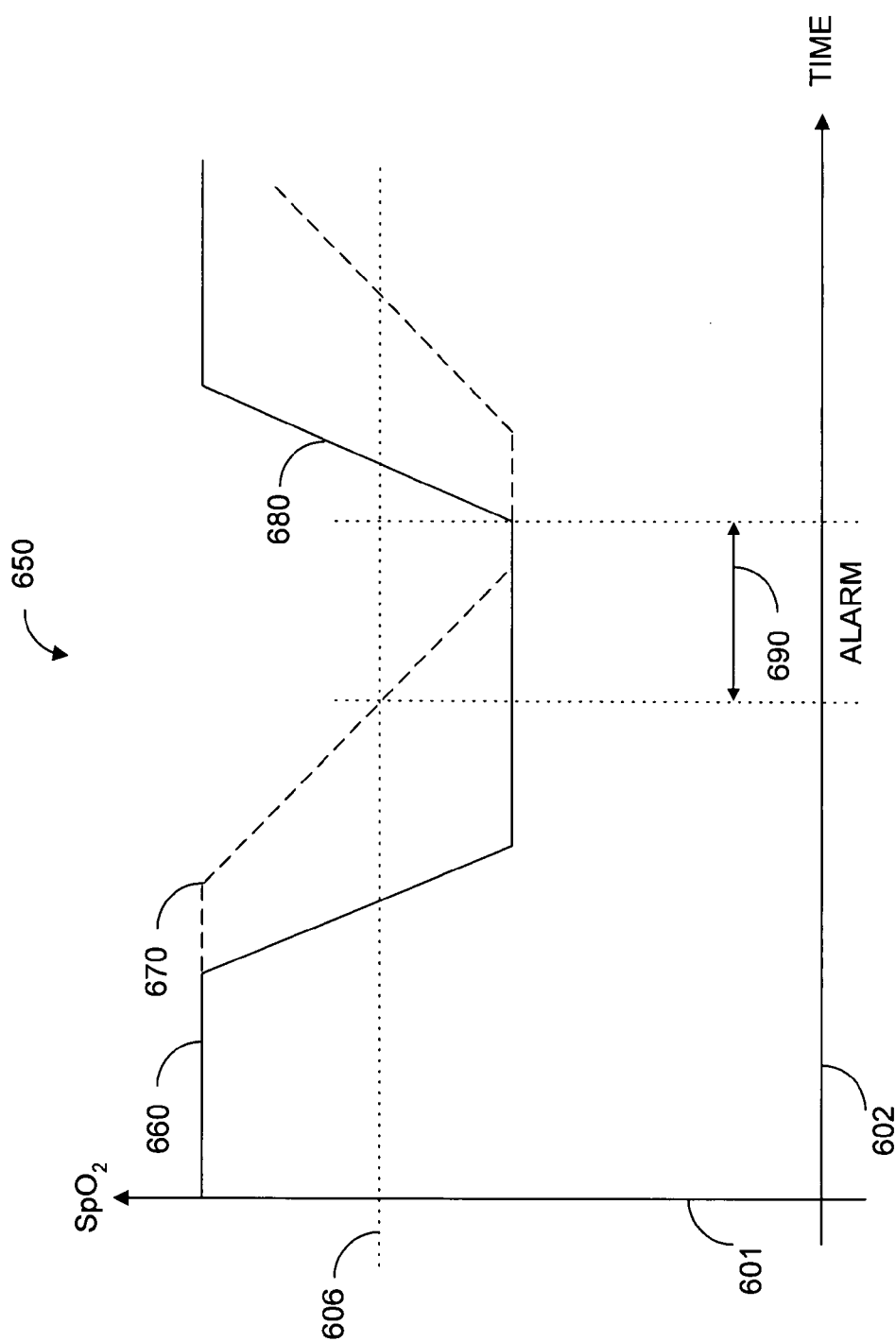

FIGS. 6A-B illustrate operation of the trend recognition alarm indicator 320 (FIG. 5). In FIG. 6A, a graph 600 has an SpO$_2$ axis 601 and a time axis 602. Shown along the SpO$_2$ axis 601 is a constant SpO$_2$ value 606 corresponding to a threshold 305 (FIG. 5). The graph 600 shows a first plot of SpO$_2$ versus time 610 corresponding to a fast SpO$_2$ measurement 422 (FIG. 5). The graph 600 also shows a second plot of SpO$_2$ versus time 620 corresponding to a slow SpO$_2$ measurement 412 (FIG. 5). A suppressed alarm interval 640 along the time axis 602 corresponds to an alarm that would be indicated by the threshold detector 510 (FIG. 5) but is suppressed as occurring during a positive slope portion 630 of a fast SpO$_2$ measurement 610. The alarm detector 530 (FIG. 5) would not assert an alarm output 303 (FIG. 5) during this interval.

In FIG. 6B, a graph 650 shows a first plot of SpO$_2$ versus time 660 corresponding to a fast SpO$_2$ measurement 422 (FIG. 5). The graph 650 also shows a second plot of SpO$_2$ versus time 670 corresponding to a slow SpO$_2$ measurement 412 (FIG. 5). An alarm interval 690 along the time axis 602 corresponds to an alarm period triggered by the alarm output 303 (FIG. 5). This alarm interval 640 occurs while a slow SpO$_2$ measurement 670 is below the threshold 606 and before a positive slope portion 680 of a fast SpO$_2$ measurement 660.

Figure 7:
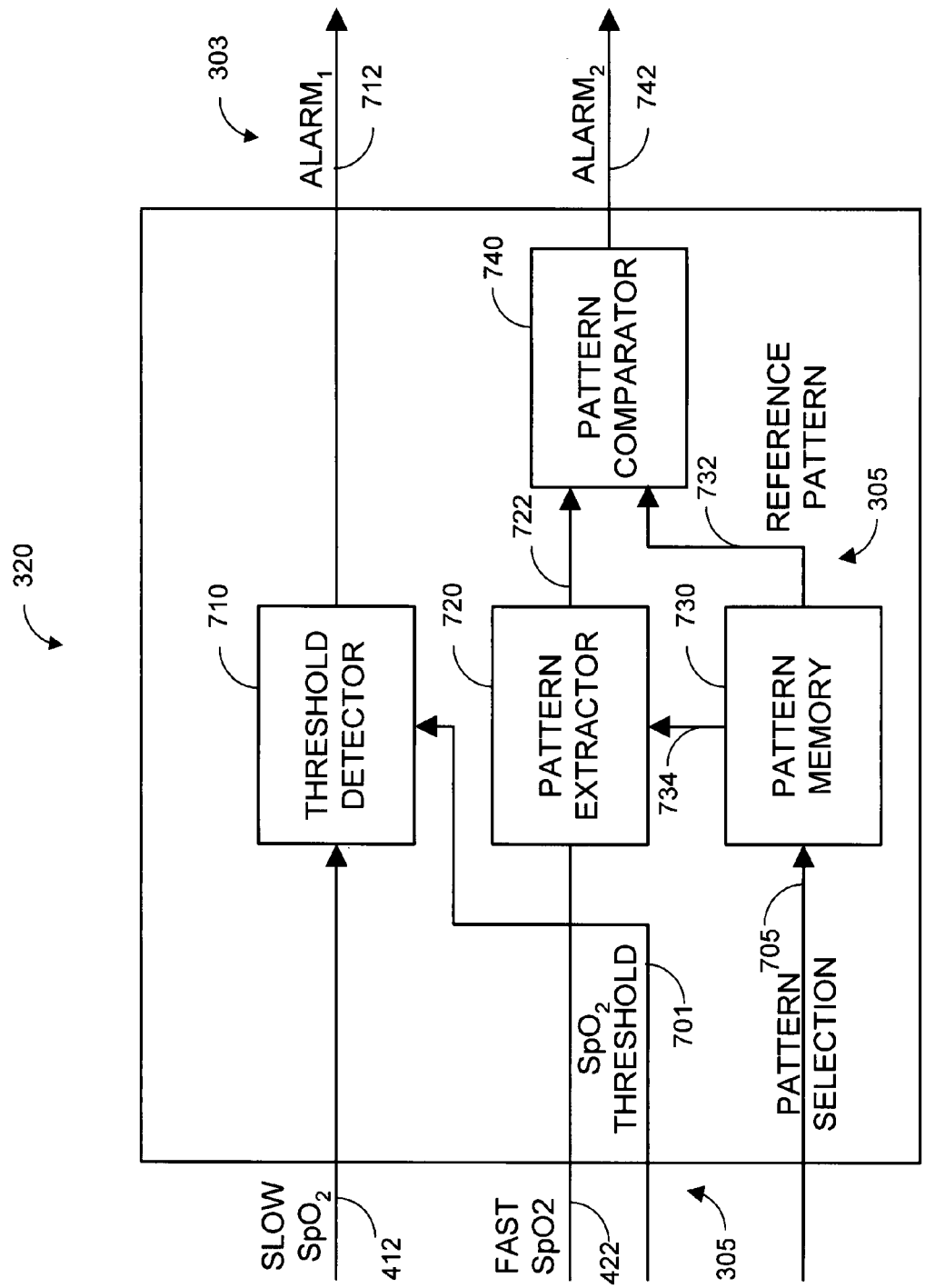
FIG. 7 is a block diagram of a pattern recognition alarm indicator utilizing a threshold detector with a slow oxygen saturation measurement input and a pattern extractor with a fast oxygen saturation measurement input.

FIG. 7 illustrates a pattern recognition embodiment of an alarm indicator 320, having a threshold detector 710, a pattern extractor 720, a pattern memory 730 and a pattern comparator 740. Further, the alarm indicator 320 has slow SpO$_2$ 412 and fast SpO$_2$ 422 measurement inputs in addition to threshold 701 and reference pattern 732 alarm condition inputs 305. The threshold detector 710 has a slow SpO$_2$ measurement 412 and a SpO$_2$ threshold 701 as inputs and a first alarm output 712. The threshold detector 710 changes the state of the first alarm output 712 when the value of the slow SpO$_2$ measurement 412 crosses the SpO$_2$ threshold 701. For example, the first alarm output 712 changes state to trigger an alarm when the slow SpO$_2$ measurement 412 becomes less than the SpO$_2$ threshold 701.

As shown in FIG. 7, the pattern extractor 720 has a fast SpO$_2$ measurement 422 and a pattern threshold 734 as inputs and an extracted pattern output 722. The pattern extractor 720 identifies features of the fast SpO$_2$ measurement 422 that may be used for pattern matching. Features may be, for example, the number of times the fast SpO$_2$ measurement 422 crosses the pattern threshold 734 within a certain time period, or the duration of each time period that the fast SpO$_2$ measurement 422 is less than the pattern threshold 734, to name a few. The pattern memory 730 has a pattern selection input 705 and a reference pattern output 732. The pattern memory 730 stores values for particular features that are identified by the pattern extractor 720. The reference pattern output 732 transfers these stored values to the pattern comparator 740. The pattern memory 730 may be nonvolatile and one or more patterns may be stored at the time of manufacture or downloaded subsequently via a data input (not shown). One of multiple patterns may be determined via the pattern selection input 705, by a user or by a separate process, for example. The pattern threshold 734 may be generated in response to the pattern selection input 705 or in conjunction with a selected reference pattern 732.

Also shown in FIG. 7, the pattern comparator 740 has the extracted pattern 722 and the reference pattern 732 as inputs and generates a second alarm output 742. That is, the pattern comparator 740 matches extracted measurement features provided by the pattern extractor 720 with selected features retrieved from pattern memory 730, changing the state of the second alarm output 742 accordingly. For example, the second alarm output 742 changes state to trigger an alarm when features of the fast SpO$_2$ measurement 422 match the reference pattern output 732. Advantageously, the pattern recognition alarm indicator 320 reduces missed events by supplementing the threshold-based first alarm output 712 responsive to the slow SpO$_2$ measurement 412 with a pattern-based second alarm output 742 responsive to detail in the fast SpO$_2$ measurement 422. In this manner, if a patient's oxygen saturation is, for example, irregular or intermittent, the second alarm output 742 may trigger a caregiver alert when the first alarm output 712 does not, as described in further detail with respect to FIG. 8, below.

Figure 8:
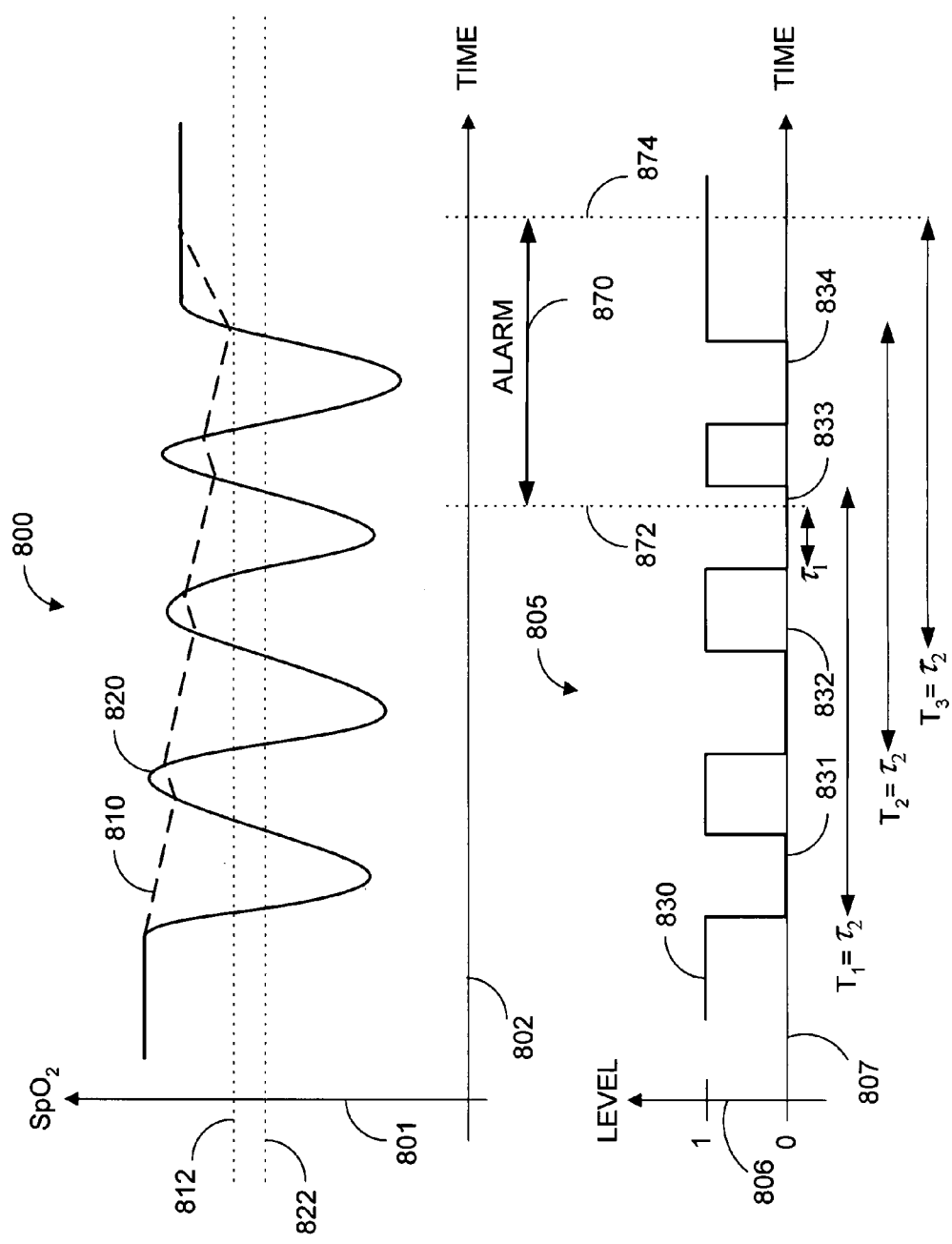
FIG. 8 is a graph of oxygen saturation versus time illustrating the pattern recognition alarm indicator according to FIG. 7.

FIG. 8 illustrates operation of a pattern recognition alarm indicator 320 (FIG. 7), as described above. A graph 800 has a SpO$_2$ axis 801 and a time axis 802. The graph 800 shows a SpO$_2$ plot versus time 810 corresponding to the slow SpO$_2$ measurement 412 (FIG. 7). Shown along the time axis 802 is a constant SpO$_2$ value 812 corresponding to the SpO$_2$ threshold 701 (FIG. 7). Due to the short duration of irregular and intermittent drops in SpO$_2$, the slow SpO$_2$ measurement 810 does not fall below the SpO$_2$ threshold 812. Thus, the first alarm output 712 (FIG. 7) does not trigger an alarm in this example.

Also shown in FIG. 8, the graph 800 shows a SpO$_2$ plot versus time 820 corresponding to the fast SpO$_2$ measurement 422 (FIG. 7). Shown along the time axis 802 is a constant SpO$_2$ value 822 corresponding to the pattern threshold 734 (FIG. 7). A corresponding graph 805 has a logic level axis 806 and a time axis 807. The graph 805 shows a logic level plot versus time 830 corresponding to the extracted pattern output 722 (FIG. 7). The logic level plot 830 has a "1" level when the fast SpO$_2$ plot 820 is above the pattern threshold 822 and a "0" level when the fast SpO$_2$ plot 820 is below the pattern threshold 822. In this manner, the logic level plot 830 indicates the number and duration of times the fast SpO$_2$ plot 820 falls below a threshold value 822.

Further shown in FIG. 8, an alarm interval 870 along the time axis 802 corresponds to an alarm period indicated by the pattern comparator 740 (FIG. 7). This alarm interval 870 occurs after a reference pattern 732 (FIG. 7) is detected as matching an extracted pattern 722 (FIG. 7) and ends, correspondingly, when there is no longer a match. For example, assume that the reference pattern output 732 (FIG. 7) has the alarm criteria that at least three below threshold periods of minimum duration $\tau_1$ must occur during a maximum period $\tau_2$, where the value of $\tau_1$ and $\tau_2$ are illustrated along the time axis 807. The below threshold time periods 831-834 are each greater in duration than $\tau_2$ and a first set of three, below-threshold time periods 831-833 occurs within a time period $T_1 = \tau_2$, as illustrated. Thus, the alarm interval beginning 872 is triggered by the second alarm output 742 (FIG. 7). A second set of three, below-threshold time periods 832-834 also occurs within a time period $T_2 = \tau_2$, as illustrated. Thus, the alarm interval 870 continues. There is no third set of three, below-threshold time periods. Thus, after the end of the time interval $T_3 = \tau_2$, the alarm interval end 874 is triggered. This example illustrates how the pattern recognition alarm indicator 320 (FIG. 7) can trigger an alarm on an event, such as a period of irregular heartbeats, that might be missed by a threshold-based alarm responsive to the slow SpO$_2$ measurement 412.

Although some alarm processor embodiments were described above in terms of pulse oximetry and oxygen saturation measurements, one of ordinary skill in the art will recognize that an alarm processor as disclosed herein is also applicable to the measurement and monitoring of other blood constituents, for example blood glucose and total hemoglobin concentration to name a few, and other physiological parameters such as blood pressure, pulse rate, respiration rate, and EKG to name a few.

In an embodiment, multiple pattern processors, each including a pattern extractor, pattern memory and pattern comparator, such as described with respect to FIG. 7, above, have as inputs one or more of fast $SpO_2$ measurements, a pulse oximeter plethysmograph and pulse rate measurements. An arrhythmia alarm is generated based upon irregular heartbeat patterns being matched or otherwise detected in one or more combinations of $SpO_2$ measurements, a pulse oximeter plethysmograph and pulse rate measurements.

A parallel alarm processor has been disclosed in detail in connection with various embodiments. These embodiments are disclosed by way of examples only and are not to limit the scope of the claims that follow. One of ordinary skill in the art will appreciate many variations and modifications.

What is claimed is:

1. A parallel alarm processor comprising:
    a sensor signal responsive to multiple wavelengths of light transmitted into a tissue site and detected after attenuation by pulsatile blood flow within the tissue site;
    a first processor having an input responsive to the sensor signal and a smoothing output responsive to relatively long duration oxygen desaturations;
    a second processor having an input responsive to the sensor signal and a predictor output responsive to relatively short duration, intermittent oxygen desaturations;
    a threshold detector responsive to the smoothing output so as to generate a first alarm when the smoothing output crosses a predetermined threshold; and
    a pattern processor responsive to the predictor output so as to generate a second alarm when a predetermined pattern is detected in a series of oxygen desaturations.

2. The parallel alarm processor according to claim 1 wherein the pattern processor comprises:
    a pattern memory storing a predetermined reference pattern;
    a pattern extractor generating an extracted pattern of oxygen desaturations from the predictor output; and
    a comparator in communications with the pattern memory and the pattern extractor so as to trigger the second alarm when the reference pattern generally matches the extracted pattern.

3. The parallel alarm processor according to claim 2 wherein the first and second processors comprise a variable mode averager.

4. A parallel alarm processor method comprising: transmitting light having multiple wavelengths into a patient tissue site;
    detecting the light after attenuation by pulsatile arterial blood flow within the tissue site so as to generate a sensor signal;
    generating a first blood oxygen saturation measurement responsive to the sensor signal and to short duration, intermittent oxygen desaturations of the patient;
    generating a second smoother blood oxygen saturation measurement responsive to the sensor signal and to long duration oxygen desaturations of the patient;
    detecting a threshold crossing of the smoother blood oxygen saturation measurement;
    recognizing a pattern in the first blood oxygen saturation measurement; and
    triggering a first alarm in response to the recognized pattern and a second alarm in response to the threshold crossing.

5. The parallel alarm processor method according to claim 4 wherein generating a first blood oxygen saturation measurement comprises predicting an oxygen saturation parameter.

6. The parallel alarm processor method according to claim 5 wherein generating a second blood oxygen saturation measurement comprises smoothing an oxygen saturation parameter.

7. A parallel alarm processor comprising:
    a threshold detector having a first output responsive to relatively long duration oxygen desaturations;
    a pattern extractor having a second output responsive to relatively short duration oxygen desaturations;
    a predetermined reference pattern indicative of a series of intermittent oxygen desaturations;
    a first alarm triggered when the first output crosses a lower limit threshold; and
    a second alarm triggered when the second output matches the predetermined reference pattern.

8. The parallel alarm processor according to claim 7 further comprising:
    an integrator inputting smoothed oxygen saturation measurements to the threshold detector; and
    a predictor inputting predictive oxygen saturation measurements to the pattern extractor.

9. The parallel alarm processor according to claim 8 wherein the integrator and the predictor are a variable mode averager.

* * * * *